(12) United States Patent
Berthold et al.

(10) Patent No.: US 6,399,091 B1
(45) Date of Patent: Jun. 4, 2002

(54) WOUND DRESSING FOR THE CONTROLLED RELEASE OF ACTIVE SUBSTANCE TO WOUNDS, AND PROCESS FOR ITS MANUFACTURE

(75) Inventors: Achim Berthold, Andernach; Walter Muller, Neuwied, both of (DE); Frank-Ulrich Flother, Schaffhausen; Rainer Naeff, Langwiesen, both of (CH)

(73) Assignee: LTS Lohamann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/584,876

(22) Filed: Jun. 1, 2000

(30) Foreign Application Priority Data

Jun. 4, 1999 (DE) .......................................... 199 25 519

(51) Int. Cl.[7] .......................... A61F 13/00; A61F 13/02; A61L 15/00; A61L 15/16
(52) U.S. Cl. ...................... 424/443; 424/445; 424/446; 424/447; 424/448; 424/449
(58) Field of Search ................................ 424/443, 402, 424/404, 444, 445

(56) References Cited

U.S. PATENT DOCUMENTS

| 4,717,717 A | 1/1988 | Finkenaur et al. ............ 514/21 |
| 5,427,778 A | 6/1995 | Finkenaur et al. ....... 424/78.08 |
| 5,457,093 A | 10/1995 | Cini et al. ..................... 514/12 |
| 5,578,661 A | 11/1996 | Fox et al. ....................... 524/27 |
| 5,591,709 A | 1/1997 | Lindenbaum et al. .......... 514/4 |
| 5,681,579 A | * 10/1997 | Freeman |
| 5,705,485 A | 1/1998 | Cini et al. ..................... 514/12 |
| 5,738,860 A | * 4/1998 | Schonfeldt et al. |
| 5,744,152 A | * 4/1998 | Capelli |
| 5,770,228 A | 6/1998 | Edwards et al. ............ 424/488 |
| 6,072,100 A | * 6/2000 | Mooney et al. |
| 6,095,996 A | * 8/2000 | Steer et al. |
| 6,171,594 B1 | * 1/2001 | Neilsen |

FOREIGN PATENT DOCUMENTS

| DK | DE 38 27 561 C1 | 8/1988 |
| DK | DE 44 46 380 A1 | 12/1994 |
| WO | WO 93/08825 | 5/1993 |
| WO | Wo 98/017252 | 4/1998 |

* cited by examiner

Primary Examiner—Thurman K. Page
Assistant Examiner—Isis Ghali
(74) Attorney, Agent, or Firm—Jordan & Hamburg LLP

(57) ABSTRACT

A wound dressing for the controlled release of active substance to wounds, especially of wound healing-promoting substances to slow-healing, chronic wounds, is characterized in that said wound dressing has a layered structure for the purpose of absorbing liquid, especially wound exudate, under volume increase, said layered structure at least comprising one polymer-containing layer (1), one woven fabric-like or nonwoven-like layer (2) and at least one active substance, and in that the polymer-containing layer (1) contains hydrocolloid-containing swellable hydrogel as absorbent for liquid.

17 Claims, 1 Drawing Sheet

Figure 1:
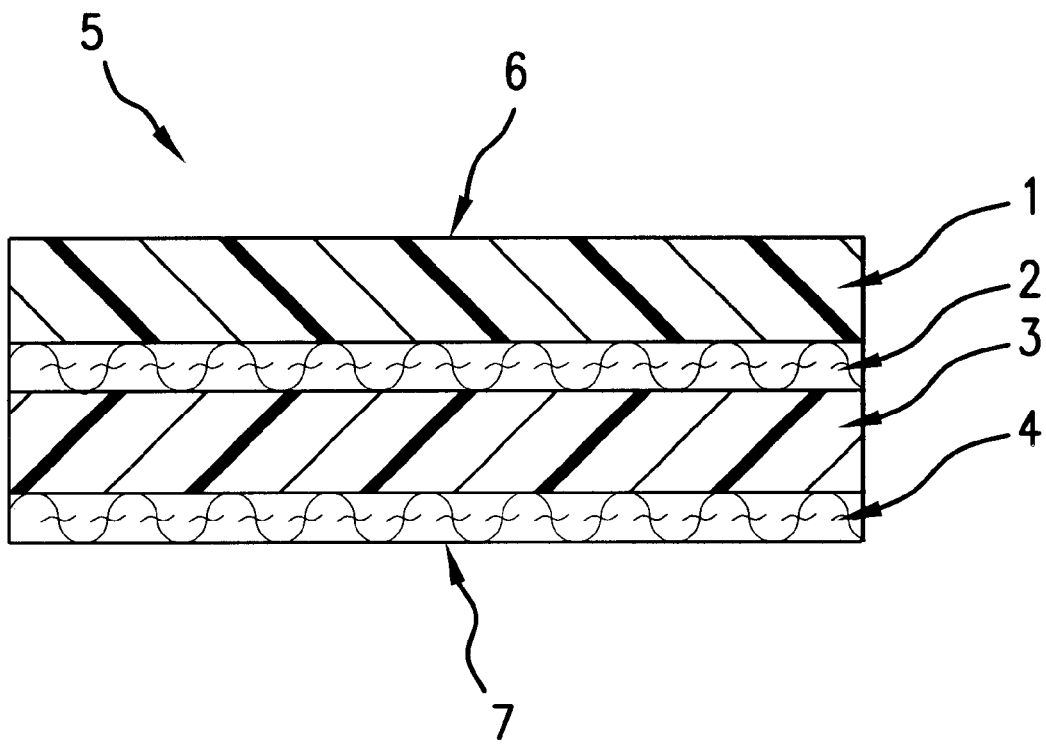

WOUND DRESSING FOR THE CONTROLLED RELEASE OF ACTIVE SUBSTANCE TO WOUNDS, AND PROCESS FOR ITS MANUFACTURE

The invention relates to a wound dressing for the controlled release of active substances to wounds, especially of wound healing-promoting substances to slow-healing, chronic wounds, as well as a process for its manufacture.

By definition, every wound that shows no tendency to heal within eight weeks is to be regarded as chronic. In current wound therapy one has to take into account the following aspects of therapy with respect to wound dressings:

The wound dressing is to create a warm and moist wound environment while largely excluding atmospheric oxygen, as wounds heal more rapidly under occlusion. As the cause for the "healing" action of an occlusive milieu the following mechanism is, inter alia, being discussed in the literature: Due to the absence of oxygen, the wound is forced to convey oxygen to the wound area via the blood. This takes place through increased pannus formation under vascularisation and thereby promoted wound healing.

In order not to disturb the wound healing process, the wound dressing should be changed only rarely since removing a fully soaked wound dressing causes a loss of components of wound exudate and thus of immunocompetent cells.

Everything the endogenic defence and purification mechanisms cannot cope with must be removed from the wound. In particular, secretion which does not run off and is possibly infected with germs entails a high risk of infection. Possibly, this negative effect is even increased by an unsuitable dressing of poor absorbent power and water vapour permeability.

Wound dressings can be classified into various groups on the basis of their properties. The following dressings are being distinguished:

Interactive wound dressings: hydrocolloids, hydrogels, alginates, polyurethane foams and films.

Active wound dressings: activated charcoal compresses or pads, silver-activated charcoal compresses or pads and iodine gauze. Through absorptive processes, they actively influence the wound climate and have a physicochemically defined mechanism of action, but only negligible absorbent power for secretion.

If one classifies according to breathing capacity, then alginates, hydrocolloid gels, hydrogels and special films belong to the gas-permeable systems, and the hydrocolloid, hydrogel and flexbible foam compresses or pads as well as the standard films belong to the semipermeable/semi-occlusive systems.

Examinations have shown that, compared to acute wounds, chronic wounds contain considerably more leucocytes and matrix metalloproteinases (MMP). Through increased MMP concentration the extracellular matrix is degraded, and, in addition, growth factors, including their recipes, are degraded at the target cells, so that the wound healing cascade is halted. By external delivery of wound healing factors, especially of growth factors, it is possible to break the vicious circle, and the wound healing cascade can restart.

The use of gels, especially of hydrogels, for treating damaged skin and wounds is described in the literature. Their use is advantageous in that they possess good biological compatibility, especially when applied for a prolonged period of time. For the production of these hydrogels, various substances, auxiliary agents and active agents are used.

Gels can be used alone or together with active agents. For example, if gels are used as such, i.e. without active agent, they serve above all to regulate the wound environment. The aim is to create a wound environment which promotes the healing of the wound. This is based on the finding that wounds heal better and more quickly under warm and humid conditions.

Gels are also used as carriers for active agents. Here, a controlled release of active substance to the wound is aimed at. Active substances or active substance groups mentioned in this context are, for example: deoxyribonucleosides, growth factors (PDGF, TGF, FGF, CGF, CTAP), protein kinase C, antibiotics, antimycotics, enzyme inhibitors, antihistaminics, antiseptics, vitamins, glucocorticoids, antiviral active substances, steroids, insulin and analgesics.

DE 38 27 561 C describes the use of flexible, hydrophile, water-swellable gel films. For the production thereof, anion-active polymers are used together with cation-active polymers. In addition, humectants, water-dispersible auxiliary agents, up to 70% of water, and active substance are contained.

DE 44 46 380 A1 describes hydrogels, for example based on gelatine, for releasing therapeutic and/or cosmetic active substances to the skin, or for cosmetic care and treatment of sensitive sites of the skin and nails. The hydrogels described are characterized by the fact that they are rigid-elastic bodies adapted to the contours of sites of the human body. These hydrogels may be characterized by a pressure-sensitive adhesive surface.

WO 98/17252 describes a water-insoluble film-forming gel having (bio)adhesive properties for local delivery of pharmaceutical active agents. Said gel contains at least one water-insoluble cellulose derivative and a non-aqueous solvent. It may be applied to skin as well as to mucous membranes.

U.S. Pat. Nos. 5,770,228, 4,717,717 and WO 93/08825 describe gels based on hydroxyethyl cellulose. These gels are used for the release of growth factors, e.g. PDGF, TGF, EGF and FGF. In addition, gels may contain a preserving agent such as, for example, methyl parabene or ethanol.

U.S. Pat. Nos. 5,705,485 and 5,457,093 describes gels for treatment of wounds. These contain effective amounts of PDGF (Platelet Derived Growth Factor). As gel formers, cellulose derivatives are used, for instance carboxymethyl cellulose. Further contained are agents carrying a load opposite to that of the PDGF. Here, amino acids such as, for instance, lysin or alanine, are mentioned, but also metal ions such as magnesium or zinc.

U.S. Pat. No. 5,591,709 describes a gel as active substance delivery system. As gel-forming components, gelatine, agrose, collagen and hydrophile cellulose derivatives are used. The system. serves to release insulin, growth hormones and thyroxine or triiodothyronine.

U.S. Pat. No. 5,578,661 describes a gel suitable for delivery of PDGF. This is an aqueous mixture of at least three components capable of gel formation. They contain a hydrophile, water-soluble polymer as component 1: polyethylene glycol, poly-vinyl pyrrolidone; an acid-containing polymer as component 2: polyvinyl pyrrolidone-polyacrylic acid copolymer, polyacrylic acid, polymethyl vinyl ether-polymaleic acid anhydride copolymer, polyethylene maleic acid anhydride; a polymer having amino groups as component 3: e.g. poly-saccharides, poly-L-lysin. The acid functions of the second component lead to cross-linking and/or form hydrogen bridges together with the first component. Here, the third component serves to accept hydronium ions. The result is a cohesive hydrogel. It is a characteristic of this system that the gel does not form spontaneously but only with time. Consequently, it is possible to initially process a low-viscous mixture. This mixture, however, gradually cures and forms a hydrogel.

U.S. Pat. No. 5,427,778 describes a gel for the release of growth factors (EGF, FGF, PDGF, TGF, NGF and IGF). As gel-former, a polymer based on acrylamide is used.

It is a substantial drawback of the described systems that they are characterized by a considerably limited swelling capacity and that upon swelling they more or less loose their shape and coherence. For this reason, it is necessary to cleanse the wound thoroughly after application of the systems to the wounds. This cleansing may lead to irritation or disturbance of the healing process. Especially when hydrocolloids and hydropolymers are used, it is possible that, despite careful cleansing, gel particles are walled off in the wound, which will possibly cause a foreign body response. This can lead to considerable complications.

Starting from the above-discussed prior art, it was the object of the present invention to provide a wound dressing for controllable release of active substance and, in particular, of wound healing-promoting substances to slow healing, chronic wounds, as well as a process for its manufacture, which wound dressing is capable of absorbing liquid under increase in volume without loosing its coherence in the process, and which moreover substantially promotes the healing process.

To achieve this object in a wound dressing for the controllable release of active substances to a wound, especially of wound healing-promoting substances, it is proposed according to the invention that said wound dressing has a layered structure for the purpose of absorbing liquid, especially wound exudate, under volume increase, said structure at least comprising one polymer-containing layer, one woven fabric-like or nonwoven-like layer and at least one active agent, and that the polymer-containing layer contains hydrocolloid-containing swellable hydrogel as absorbent for liquid.

Advantageously, by means of the configuration of the wound dressing according to the invention, it is achieved that on the one hand said wound dressing is able to absorb liquid such as wound exudate in larger amounts under volume increase without loosing its coherence, and that on the other hand by means of said wound dressing, wound healing-promoting substances are delivered to the wound, thereby inducing an accelerated healing process, especially by providing the healing-promoting occlusion of the wound, said healing process making the frequent changing of the dressing superfluous.

The active substance-containing wound dressing advantageously contains hydrocolloid-containing hydrogels which, on account of their swelling capacity, are able to absorb liquid while maintaining their coherence. The colloid portion of the wound dressing gradually binds the exudate under transformation into a free gel which lines the wound and its recesses. In contrast thereto, the hydrogel forms a coherent matrix which has a swelling effect especially in dry wounds, and which dissolves coats as well as necroses.

The active substance-containing wound dressing according to the invention moreover serves to release growth factors to slow-healing, chronic wounds. Examples of growth factors to be mentioned are: PDGF (Platelet Derived Growth Factor), rhPDGF-BB (Becaplermin), EGF (Epidermal Growth Factor), PDECGF (Platelet Derived Endothelial Cell Growth Factor), aFGF (Acidic Fibroplast Growth Factor), bFGF (Basic Fibroplast Growth Factor), TGF α (Transforming Growth Faxtor alpha), TGF β (Transforming Growth Factor beta), KGF (Keratinocyte Growth Factor), IGF1/IGF2 (Insulin-Like Growth Factor) and TNF (Tumor Necrosis Factor).

Substantial embodiments of the wound dressing according to the invention are provided according to the features of the subdlaims, which also stipulate the active agents and auxiliary agents contained in the individual layers.

The wound dressing according to the invention will be explained in the following in greater detail by means of an embodiment example shown in FIG. 1, and the manufacture thereof will be explained by way of example.

FIG. 1 shows a section, transverse to the upper and lower sides, of the individual layers of a conventional embodiment of the wound dressing.

The wound dressing comprises four layers (1–4), namely two polymer-containing layers (1) and (3), and two nonwoven-like or woven fabric-like layers (2) and (4), respectively. Altogether, they form a matrix (5) having an upper side (6) and a lower side (7).

The matrix (5) thus formed may be applied with both the upper layer (6), which may have adhesive properties, as well as with the lower side (7), which typically is nonadhesive.

For the manufacture of the polymer-containing layer, all known biocompatible polymers may be used. To be mentioned in this context are, in particular, polyethylene glycol derivatives, polivinyl pyrrolidone derivatives, polymers of acrylic or methacrylic acid, silicones, polyisobutylenes, polyisoprenes, polystyrenes and similar substances.

The matrix is able to absorb a quantity of liquid (such as water or exudate) which is many times larger than its own weight and to swell correspondingly. Its absorptive capacity is ensured by means of the incorporated absorber. Suitable absorbers are, for example, polymers such as cellulose or starch derivatives (for example, carboxymethyl cellulose, hydroxyethyl cellulose, hydroxypropyl cellulose, hydroxypropyl methyl cellulose, carboxymethyl starch and others), as well as polyacrylic acid derivatives (e.g. Aquakeep), but also low-molecular compounds such as glycerol, sorbite or PEG 400.

The coherence of the dressing is ensured by means of the inlayed nonwoven or woven fabric. Suitable materials to be employed as nonwoven or woven fabric are, for instance, those based on polyurethane, polyester, cellulose or others.

In the following, the invention will be explained by way of example by means of an example of the manufacture of a wound dressing containing a growth factor, namely PDGF.

The active substance-containing wound dressing is manufactured in a two-stage process. To this end, initially, the actual wound dressing is manufactured employing techniques known from the manufacture of patches. In a second step, the active substance is added to the dressing in form of a solution. To produce the actual wound dressing, carboxymethyl cellulose is dispersed in an organic solution consisting of polyvinyl pyrrolidone, PEG 400 and ethanol. This mixture is applied in a defined layer thickness to a siliconized poly-ester film by means of an applicator unit, and dried at 60° C. for 30 minutes. The dried film corresponds to the polymer-containing layer (1), as shown in FIG. 1. After the drying process, a woven fabric (2) of polyester is laminated onto the polymer-containing layer (1). A "bilayer" is obtained as a result. For preparing the "multilayer" shown in FIG. 1, the siliconized polyester film is removed and the upper side of the polymer-containing layer (1) of a "bilayer"

is laminated onto the lower side of the polymer woven fabric (3) of a second "bilayer". The result is a wound dressing consisting of four layers (1–4). As already mentioned, following the manufacture of the actual wound dressing (5), the PDGF-containing solution is either added to the polymer-containing layer (1) or to the polyester woven fabric (3).

Optionally, one may also prepare a sterile PDGF-containing wound dressing. Since PDGF is sensitive to conventional sterilisation methods, the manufacture must take place under aseptic conditions. To this end the actual wound dressing (5) is initially prepared as described above, and subjected to a conventional temperature-neutral sterilisation method, preferably gamma sterilisation. Subsequently, the active substance solution is added to the wound dressing (5) under aseptic conditions, for instance employing a so-called Laminar Flow Box, and is thereafter packed under aseptic conditions.

The wound dressing according to the invention shown in FIG. 1 in section comprises four layers (1–4), namely the polymer-containing layers (1) and (3), as well as the nonwoven-like and woven fabric-like layers (2) and (4), respectively. The polymer-containing layer (1) forms the upper side (6) and the woven fabric-like or nonwoven-like layer (4) forms the lower side (7). One of the upper and lower sides (6) and (7), respectively, may be pressure-sensitive adhesive.

In the following, the aseptic production method will be explained in detail, which is necessary where active substances are used which are sensitive to conventional sterilisation methods.

In the process according to the present invention, an active substance carrier is prepared, said active substance carrier is subjected to a sterilisation process and is equipped with at least one active substance under aseptic conditions.

The manufacture of the active substance carrier is carried through according to known techniques. As active substance carriers, all types of wound dressings are possible. Examples to be mentioned here are:

inactive sound dressings (gauze compresses or pads, swabs, viscose-gauze compresses or pads and suction nonwoven compresses/pads) which cause no change on the cellular and substantial level, that is they merely absorb more or less secretion, interactive wound dressings (hydrocolloids, hydrocolloid compresses/pads, hydrogels, hydrogel compresses/pads, alginates, polyurethane foam and poly-urethane films) which change the micro-climate in the wound, create a physiological environment, accelerate the healing process, suck off the secretion and store it, active wound dressings (activated charcoal compresses or pads, silver-activated charcoal compresses or pads and iodine gauze) which intervene in the wound climate by cytopathogenetic/adsorptive progresses, and which have a chemically/physically defined/specific mechanism of action; they generally possess only negligible absorbent power, gas-permeable systems (alginates, hydrocolloid gels, hydrogels and special films) having considerably higher breathing than the skin. They have a broad scope of indication and can also be used in infected wounds.

After manufacture of the active substance carrier it is subjected to a conventional sterilisation method the selection of which is dependent above all on the product which is to be sterilized. Since generally the number of microorganisms dying per unit of time under constant conditions in a sterilisation process is dependent on the originally present number of organisms capable of living, the initial number of organisms present in each case is of great significance. The sterilization process is, however, not only influenced by the initial number of germs but to an even greater extent by the type of microorganisms present as well as their functional status. The selected method must have a sufficient degree of effectiveness. Standard methods are sterilisation with live saturated steam (15 min, 2 bar, 121° C.), sterilisation by means of dry heat (30 min, 180° C.), radiation sterilisation, gas sterilisation.

Suitable equivalent or alternative methods may be used as well.

The active substance is added to the active substance carrier under aseptic conditions. This addition may be performed, for example, in form of a solution, with the active substance being dissolved in sterilised water, an autosterile solvent mixture or any other suitable carrier.

"Aseptic conditions" is understood to mean the strict prevention of germs entering during the manufacturing process. Since aseptic preparation does not include the final sterilisation in the final container, which is closed in a bacteria-proof manner, it is not considered a sterilisation method. Apart from a painstakingly thorough production hygiene and exact disinfection of rooms and room air, so-called "clean rooms" are considered a precondition for aseptic processes. The term "clean rooms" refers to rooms or certain areas in rooms wherein, by means of filtration of the air, the degree of contamination has been reduced to at most 3.5 particles$\geq 0.5$ $\mu$m per liter of air. Considering that in 1000 particles of dust one has to expect one organism, in such rooms one organism is present in about 3 $m^3$. The air filtration is carried through by guiding the air in such a way that at a rate of about 0.5 m/sec an air stream, which is as laminar as possible, expels all suspended particles from the scanned space. In this way, "clean areas" can be created in otherwise normally clean rooms. The aseptic work is then carried out within the clean areas while the operating personnel moves outside those areas and represents a danger of contamination only in case of inappropriate behaviour.

The process according to the invention will in the following be described with reference to the aseptic manufacture of active substance-containing hydrogels.

Hydrogels are moist dressings absorbing water through swelling and releasing water by deswelling. They consist of higher-molecular molecules forming a coherent matrix which encloses smaller molecules and aqueous solutions. These gels are extremely consistency-stable.

The manufacturing process comprises the following steps:

Preparing a hydrogel-based active substance carrier; two examples of embodiments will be described in the following:

a) Preparing a uni-laminate: polyvinyl pyrrolidone (2.7%-wt.) is dissolved in purified water (34.4%-wt.), and glycerine (26.7%-wt) as well as gelatine (15.5%-wt.) are added. The solution is allowed to swell for 10 min. and is thereafter heated to 65° C. until clear. To this solution are added saccharose (10.7%-wt.) and dexpanthenol (10%-wt.), one after the other, while stirring continuously. The homogenized solution is subsequently applied to a suitable film or filled in suitable containers (e.g. thermoforming sheets) and is left to set.

b) Preparation of a multi-laminate: carboxymethyl cellulose is dispersed in an organic solution consisting of polyvinyl pyrrolidone, PEG 400 and ethanol. This mixture is applied in a defined layer thickness to a siliconized polyester film by means of an applicator unit and dried at 60° C. for 30 minutes. In the following, the dried layer will be referred to as the polymer-containing layer. Following the drying process, a polyester woven fabric is laminated onto the surfaces of the polymer-containing layer, thus producing a "bi-layer". For preparation of a multi-laminate, the siliconized polyester film is removed and the upper side of the polymer-containing layer of one "bi-layer" is laminated onto the lower side of the woven polymer fabric of a second "bi-layer". The result is a wound dressing consisting of four layers.

Separation of partial amounts
  If the hydrogel is applied sheet-like to a film, individual punched pieces of hydrogel are subsequently punched out employing a suitable punch, and these are conveyed to suitable containers (e.g. thermosetting sheets), Sterilisation method
  Sterilisation of the rigid hydrogel is performed by means of ionised rays (radiation sterilisation). Preferably, gamma rays are used as these have a great depth of penetration and interact only slightly with the material to be sterilized. The dose to be applied (e.g. 25 kGy) depends on the microbiological starting conditions (F=n×D). As radiation source, the radionuclide $^{60}$Co is typically used.

Equipping the active substance carrier with active substance
  The active substance (e.g. PPDGF) dissolved in sterilised water is dosed to the sterilised hydrogel, so that the active substance solution evenly wets the surface of the active substance carrier and is absorbed thereby.

Final packaging
  The hydrogels equipped with active substance carrier and active substance solution are subsequently packaged, so that sufficient protection from microbiological recontamination is guaranteed.

What is claimed is:

1. A wound dressing having a layered structure for the controlled release of active substance to wounds comprising:
  two polymer-containing layers each comprising a hydrocolloid-containing swellable hydrogel as an absorbent;
  two woven layers; and
  at least one active substance in at least one of the layers, the polymer-containing layers and the woven layers being superposed in alternating sequence.

2. The wound dressing of claim 1 wherein at least one of the polymer-containing layers contains at least one polyethylene glycol derivative.

3. The wound dressing of claim 1 wherein at least one of the polymer-containing layers contains at least one polymer based on vinyl pyrrolidone.

4. The wound dressing of claim 1 wherein at least one of the polymer-containing layers contains at least one polymer based on acrylic and/or methacrylic acid.

5. The wound dressing of claim 1 wherein at least one of the polymer-containing layers contains at least one polymer based on silicone.

6. The wound dressing of claim 1 wherein at least one of the polymer-containing layers contains at least one polymer based on isobutylene, isoprene or styrene.

7. The wound dressing of claim 1 wherein the absorbent is a polymer.

8. The wound dressing of claim 7 wherein the polymer is a cellulose derivative or a polyethylene derivative or a starch derivative.

9. The wound dressing of claim 8 wherein the cellulose derivative is carboxymethyl cellulose.

10. The wound dressing of claim 1 wherein the active substance is a biologically active peptide or protein.

11. The wound dressing of claim 10 wherein the biologically active peptide or protein is a growth factor.

12. The wound dressing of claim 11 wherein the growth factor is Platelet Derived Growth Factor.

13. The wound dressing of claim 11 wherein the growth factor is Becaplermin, Epidermal Growth Factor, Platelet Derived Endothelial Cell Growth Factor, Acidic Fibroblast Growth Factor, Basic Fibroblast Growth Factor, Transforming Growth Factor alpha, Transforming Growth Factor beta, Keratinocyte Growth Factor, Insulin-Like Growth Factor 1 or 2, or Tumor Necrosis Factor.

14. The wound dressing of claim 1 wherein the woven layer is based on polyester, polyurethane or cellulose.

15. The wound dressing of claim 1 wherein a surface thereof which is intended for application possesses adhesive properties.

16. The wound dressing of claim 1 wherein at least one of the polymer-containing layers contains 40 to 80 wt. % of polyvinyl pyrrolidone, 15 to 45 wt. % of polyethylene glycol 400, and up to 40 wt. % of sodium carboxymethyl cellulose and the at least one active substance comprises becaplermin.

17. The wound dressing of claim 1 wherein at least one of the polymer-containing layers contains 60 wt. % of polyvinyl pyrrolidone, 35 wt. % of polyethylene glycol 400, and 5 wt. % of sodium carboxymethyl cellulose and the at least one active substance comprises becaplermin.

* * * * *